United States Patent [19]
Syrop et al.

[11] Patent Number: 5,183,057
[45] Date of Patent: Feb. 2, 1993

[54] FLUID MOTION DEVICE (FMD) FOR EXERCISING THE TEMPOROMANDIBULAR JOINT

[76] Inventors: Steven B. Syrop, 36 Aldridge Rd., Chappaqua, N.Y. 10514; Howard Israel, 47 Park Cir., Great Neck, L.I., N.Y. 11024

[21] Appl. No.: 738,105

[22] Filed: Jul. 30, 1991

[51] Int. Cl.$^5$ .................. A61G 15/00; A61C 5/14; A61C 19/04
[52] U.S. Cl. ..................: 128/845; 128/861; 433/69
[58] Field of Search .............. 128/859–863, 128/62 A; 433/229, 69; 446/197, 198

[56] References Cited

U.S. PATENT DOCUMENTS

| | | | |
|---|---|---|---|
| 2,566,557 | 9/1951 | Danielson | 128/863 |
| 3,315,672 | 4/1967 | Cunningham | 128/863 |
| 3,545,125 | 12/1970 | Kisaburo | 446/197 |
| 3,625,207 | 12/1971 | Agnew | 128/863 |
| 3,997,157 | 12/1976 | Meyer | 446/197 |
| 4,174,588 | 11/1979 | Clanton | 446/197 |
| 4,928,710 | 5/1990 | Campbell | 128/861 |
| 4,932,867 | 6/1990 | Ueno | 433/69 |

*Primary Examiner*—Michael A. Brown
*Attorney, Agent, or Firm*—Frishauf, Holtz, Goodman & Woodward

[57] ABSTRACT

A method and apparatus are disclosed for exercising small joints such as the temporomandibular joint connecting the upper and lower jaws, fingers and toes of a user. First and second members are coupled together so that at least one of the members is movable relative to the other member. An expandable and contractible fluid reservoir is positioned between the first and second members so that the first and second members will move relative to each other as the expandable and contractible reservoir expands and contracts. At least one of the members is then positioned to exercise the joint specifically to exercise the jaw, the user will place the first and second members gently into the mouth and then squeezing a fluid source connected to the expandable and contractible reservoir to expand and contract said reservoir thereby moving the jaws or joint to be exercised.

42 Claims, 3 Drawing Sheets

FLUID MOTION DEVICE (FMD) FOR EXERCISING THE TEMPOROMANDIBULAR JOINT

BACKGROUND OF THE INVENTION

1. Field of the Invention

This invention relates generally to joint exercising apparatus and more particularly to jaw exercising apparatus for use in exercising the jaws of patients who suffer from Temporomandibular Joint (TMJ) problems.

TMJ problems are relatively common in the general population. Epidemiological studies have provided evidence that anywhere from 3 to 18% of the population developed symptoms characteristic of temporomandibular joint disorders at some time in their lives.

2. Description of the Prior Art

It is known from the prior art that continuous passive motion (CPM) can be used to manage joint disorders including the temporomandibular joint. Joint motion provides cartilage nutrition, stimulates regeneration of articular cartilage and reduces pain and edema. Motion is extremely important to normal joint physiology. Motion permits maintenance of healthy articular cartilage by allowing nutrients in the synovial fluid to diffuse through the surface. It has been shown that motion is also extremely important in the prevention of adhesions in the joint following injury or surgery. Motion has also been shown to reduce pain and edema in a joint that has undergone surgery or trauma. Gradual mobilization exercises have been used to help regain normal range of motion in patients with myalgia and myositis of the masticatory muscles. Specifically exercising the TMJ is beneficial:

- following temporomandibular joint surgery to reduce adhesions, pain and edema and to increase the range of motion;
- following intermaxillary fixation (jaws wired closed) in patients treated with jaw fractures or orthognathic surgery, to increase the range of motion and reduce pain and edema;
- following treatment of facial infections that result in reduced jaw opening;
- following acute trauma (blow to the jaw) or chronic trauma (grinding or clenching of teeth) to the joint, to reduce pain, edema, encourage cartilage nutrition and restore normal range of motion; and
- if the patient suffers from myositis and myalgia, to gradually restore the range of motion.

Temporomandibular joint exercisers known in the prior art were directed to mechanical and electro mechanical, relatively complex bulky devices which were expensive and frequently required individual adjustment of the device to fit a person's mouth, thus limiting use of such exercisers to non-routine TMJ problems.

SUMMARY OF THE INVENTION

An object of the present invention is to provide a fluid motion device (FMD), that is a passive motion device, that provides controlled motion to the temporomandibular joint as well as the surrounding soft tissues, muscles, tendons and ligaments.

Another object is to provide such a device which uses an hydraulic mechanism which permits gentle gradual control of jaw movement and enables biofeedback to insure that the temporomandibular joint movement is controlled by the patient within a predetermined limited range of movement.

A further object of the present invention is to provide a safe simple method for exercising small joints and to provide a simple, inexpensive fluid motion device (FMD) for use in exercising small joints (such as fingers, toes and the TMJ) that can be used readily by a patient, practitioner or physical therapist at home, or, in a medical or dental office and in a variety of other situations, and wherein the method and apparatus prevents the patient from being injured by utilization of the method and apparatus.

Another object of the present invention is to provide a simple, inexpensive light weight passive motion device that can be used by most patients without requiring individual adjustments. The jaw exerciser could be sold by prescription; the hand exerciser could be sold over the counter, possibly without prescription for finger exercisers for patients suffering from arthritis and other small joint problems.

DESCRIPTION OF THE EMBODIMENTS

Figure 1:
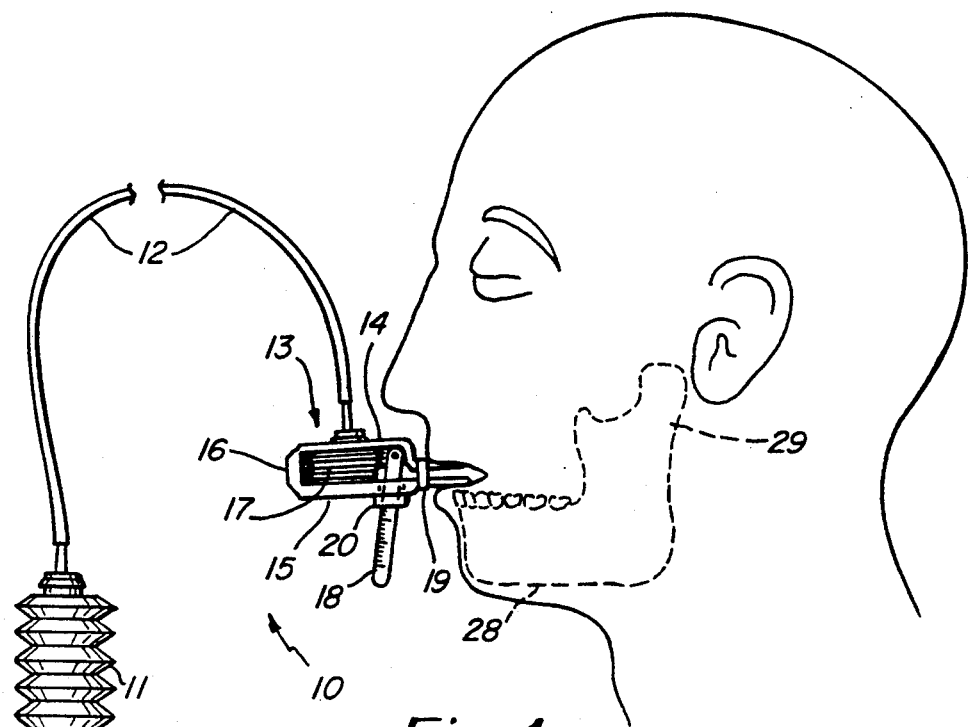
FIG. 1 is a side schematic view in elevation, showing an apparatus of the present invention for use in connection with TMJ, and the positioning of the apparatus in the mouth of a user or patient.

FIG. 1 discloses the components of the hydraulic mechanism of the present invention when positioned to exercise the temporomandibular joint (TMJ) of a person.

Figure 2:
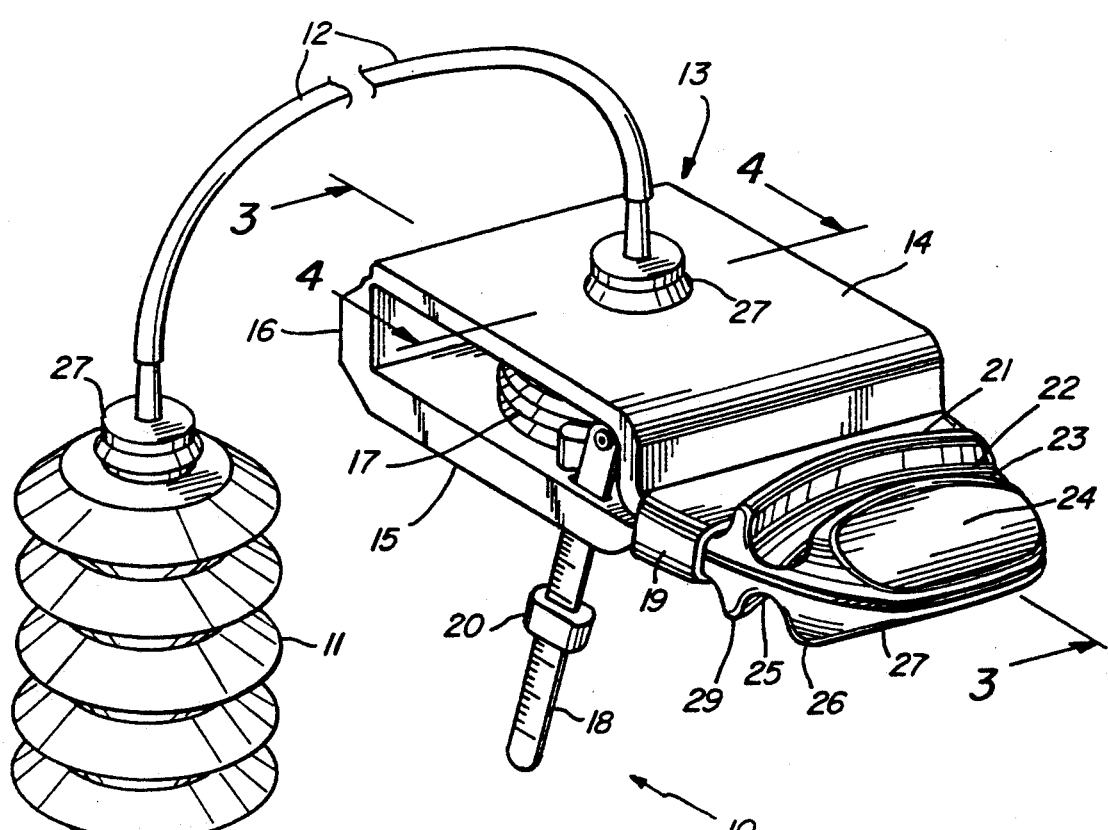
FIG. 2 is a perspective view of the hydraulic mechanism of the present invention.

Referring to FIGS. 1 and 2 the hydraulic apparatus 10, includes the following principal components: a fluid source 11; a flexible tube 12 in fluid communication with the fluid source 11 attached to fluid source 11 at one end thereof by coupling 27; and a motion control apparatus 13 attached to the other end of said flexible tube 12 by another coupling means 27. The motion control apparatus 13, includes an upper member 14 and a lower member 15, which are pivotally connected together at one end thereof by hinge portion 16. A flexible expandable bellows 17 is positioned between the upper and lower members and is in fluid communication with the flexible tube 12 via the coupling 27. The coupling 27 can screw onto a corresponding threaded portion on fluid source 11 and bellows 17 or upper member 14. The fluid source 11 can be a bellows, or any other shape which can facilitate controlled squeezing. The couplings 27 can be unscrewed to fill the device 10 with a fluid. Device 10 is preferably formed from a moldable plastic. The fluid source 11 and tube 12 and bellows 17 can be filled with a fluid and then permanently sealed to each other to provide a fluid-tight fluid path which never has to be refilled. The fluid source 11 may be replaced with an infusion pump (see FIG. 9) to permit continuous passive motion in the intermediate post operative period for a hospitalized patient. Adjustable measurement means, such as ruler 18 can be positioned and fastened to upper member 14 to facilitate measurement of the maximum permissible mouth opening for the particular patient. Ruler 18 has stop means 20 for selecting the maximum permissible opening for the mouth, of the patient or user, and to act as a stop to prevent further opening of the mouth. An elastic member 19 holds the upper member 14 and the lower member 15 together on the side of motion control apparatus 13, which is the side opposite from hinge portion 16.

As shown in FIG. 2, an integral portion of the upper member 14 is the end portion thereof which has formed thereon a first ridge 21 and a second ridge 23, which are separated by a recess 22. The two ridges and recess are shaped to accommodate the upper teeth of the patient when positioned in the mouth. A sloping ramp portion 24 at the free end of the upper member is designed to generally fit into the mouth of a patient or user, behind the front teeth. Similarly, the lower member 15 has an extended integral free end portion thereof (at the end away from the hinge 16), which includes a first ridge 29, a second ridge 26, and a recess 25 formed between the ridges 24 and 26. The ridges 24 and 26 with the intervening recess 25 are shaped to accommodate and retain the lower teeth of the patient or user when the motion control apparatus is positioned in the mouth. The front free end portion of the lower member includes a sloping portion 27, shaped to generally fit into the mouth of a patient or user when the motion control apparatus is positioned in the patient's mouth.

In operation, when the FMD is in the closed position (as shown in FIG. 2), the patient gently slides the device into his/her mouth along gently inclined ramps 24 and 27 until the upper and lower teeth fit into recesses 22 and 25. The fluid source 11 and bellows 17 and tubing 12 are then filled with fluid (if they were not permanently or previously filled) and the patient holds the fluid source (bellows) 11 in one hand. By squeezing the bellows 11 fluid is transferred to bellows 17 located between the upper and lower members of the FMD and thus, causes a gentle, fluid controlled separation of the lower jaw from the upper jaw. Since the patient is controlling the motion of the fluid, which is gradual, sudden jaw movement is avoided, preventing injury to the joint and surrounding structures. The elastic means 19 holding the free ends of the upper and lower members together, permits a passive return of the jaws to a closed mouth position. The fluid source 11 is filled with a fluid preferably water, and is coupled to tube 12 with a coupling device 27. The tube 12 is in fluid communication with the fluid source 11. The other end of tube 12 is coupled to the motion control apparatus 13 by another coupler 27 which, in turn, is in fluid communication with bellows 17 such that fluid, can move from the fluid sources 11 through the tube 12 to the bellows 17, and in the reverse direction from the bellows 17 through the tube 12 back into the fluid source 11 when pressure on fluid source 11 is released and the elastic means 19 passively returns members 14 and 15 to their original unseparated position.

In operation, when the fluid source 11 is filled with a fluid, pressure exerted on the fluid source 11 by the patient or user will force fluid through the tube 12 into the bellows 17. The bellows because of the hinge portion 16 can only open, as shown in 3, to separate the top member 14 and bottom member 15. The maximum opening between the top and bottom members is measured by the ruler 18 and guide 20 slidable on ruler 18. When the exerted pressure is released on the fluid source 11 the elastic means 19 positioned to hold the upper and lower members 14 and 15 together will exert a force sufficient to close the gap between the members created when fluid was forced into bellows 17. This action by the elastic member 19 in combination with the return of fluid source 11 to its original shape will allow fluid to flow out of bellows 17 back into the fluid source 11 until pressure is, again, exerted on the fluid source 11 by the patient or user. When pressure is exerted and released repeatedly on the fluid source 11, shown in FIG. 1, the lower jaw of the patient, schematically shown at 28, will move relative to the upper jaw which, in turn, will cause the mouth of the patient to repeatedly open and close, thereby exercising the temporomandibular joint schematically shown at 29 in FIG. 1.

Figure 3:
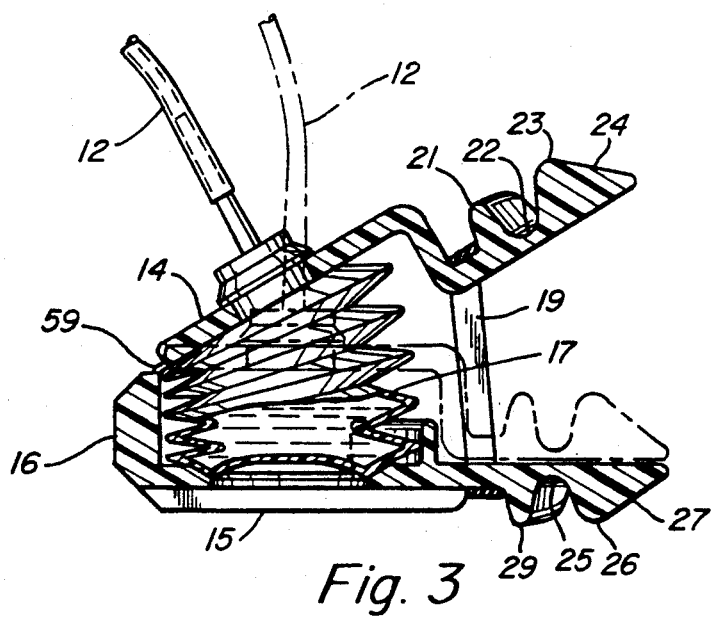
FIG. 3 is a sectional view taken along line 3—3 in FIG. 2 of the bellows portion of the present invention which is used to separate the jaws of the patient or user.

In FIGS. 1 and 2, maximum movement of the upper and lower members 14 and 15 is measured by the ruler 18 and guide 20. FIG. 3 is a sectional view of the motion control apparatus 13 of FIGS. 1 and 2, taken along the line 3—3 in FIG. 2. The solid line showing of upper member 14 in FIG. 3 shows the upper member 14 in its open position. The dashed lines in FIG. 3, show the upper member 14 when it is in its closed position relative to lower member 15.

Hinge 16, which can also be a living hinge, connects upper member 14 and lower member 15, together and permits relative movement of said members 14 and 15 relative to each other. Portion 59 of hinge 16 can be a hinge member attached on one side to upper member 14 and on the other side to hinge portion 16 to enable the upper member to move relative to the hinge portion 16 and lower member 15. As shown in FIG. 3 hinge portion 16 is fixed to member 15 to prevent movement therebetween. Portion 59 may be made of a plastic material which is fixed or otherwise attached to upper member 14 and which flexes as upper member 14 is moved relative to hinge portion 16.

Figure 4:
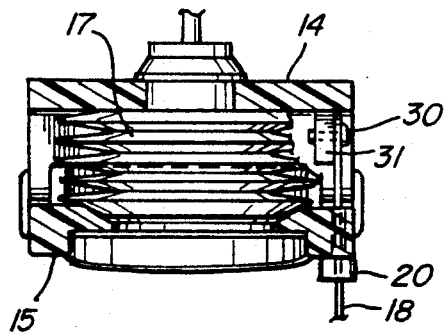
FIG. 4 is a sectional view taken along line 4—4 in FIG. 2.

FIG. 4, is a sectional view of the motion control apparatus 13 taken along the line 4—4 in FIG. 2. In FIG. 4, the upper member 14 and the lower member 15 are in the closed position. In FIG. 4, the mounting means 30 for mounting ruler 18 on upper member 14 is schematically shown as a rivet or pin 30; however, other mounting means such as a screw and nut may be used.

Figure 5:
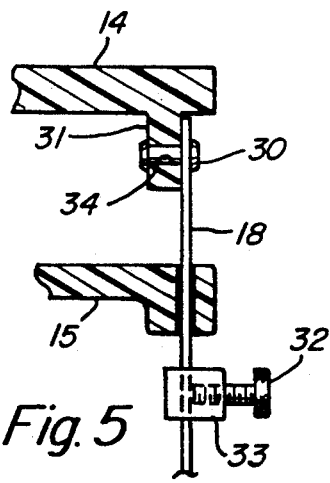
FIG. 5 is a sectional view of an alternate stop device for limiting the maximum opening provided by the hydraulic mechanism of FIG. 2.

FIG. 5 shows an alternate embodiment for the ruler 1 of FIGS. 1 and 2 mounted on upper member 14 and lower member 15. As shown in FIG. 5, the upper member 14 has a projecting portion thereof 31 formed integrally therewith. The rivet 30 or the like is mounted through the upper end of the ruler 18 through an aperture 34 formed in projection 31 of upper member 14 and a rivet or pin 30 is mounted in the aligned apertures. The ruler 18 slidably fits through an aperture formed in lower member 15; a slide 33 is mounted on ruler 18, and a thumbscrew 32 fits into an aperture in slide 33 which cooperates to set the maximum opening position for upper and lower members 14 and 15. Thumbscrew 32 and slide 33 are alternates to the ruler 18 and guide 20 shown in FIGS. 1 and 2. Alternately, guide 20 may be provided with a stop means to prevent guide 20 from moving.

Figures 6, 7:
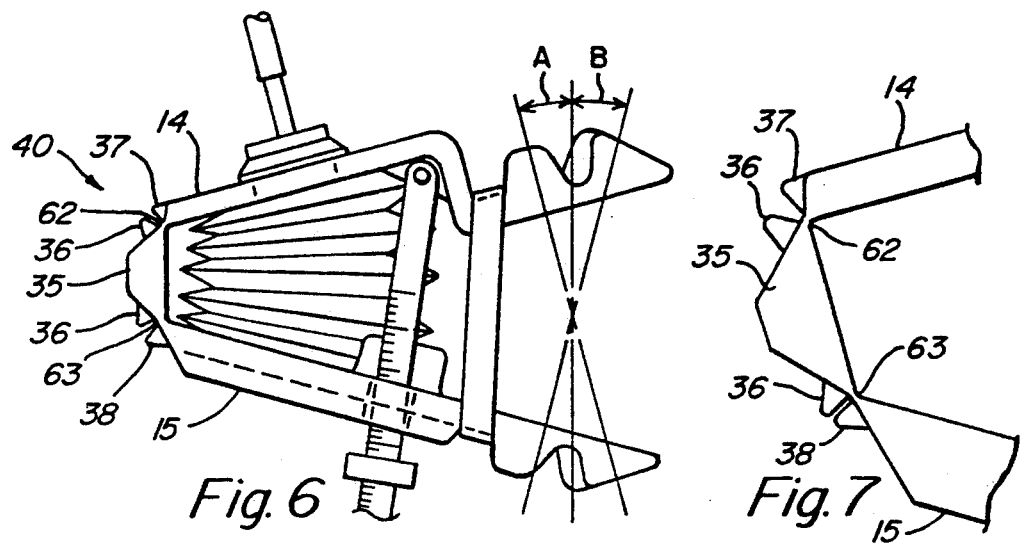
FIG. 6 is a schematic view of an alternate hinge mechanism for the hydraulic bellows shown in FIG. 3, which has a double hinge to enable the apparatus to compensate for overbite or underbite or a patient or user.
FIG. 7 is a schematic view of the double hinge mechanism of FIG. 6, which shows the details of the protrusions on each of the double hinges to limit maximum movement of the bellows relative to the hinges.

FIG. 6 discloses an alternate hinge 40 for the hinge 16 shown in FIGS. 1 and 2. In FIG. 6, the hinge 40 comprises a central member 35. Hinge means 62 connects upper member 14 to the central member 35; hinge means 63 connects lower member 15 to central member 35. This configuration provides a double acting hinge means 40 which permits movement respectively by upper member 14 and lower member 15 in both the horizontal and vertical planes. Movement laterally permits the motion control apparatus 13, to move within the motion limits A and B shown in FIG. 6 for hinge means 62, 63 to accommodate for overbite or underbite of a patient without individual adjustment. Central member 35, and hinge means 62, 63, may be formed integrally with each other as well as integrally with the upper member 14 and lower member 15. Protrusions 37 and 38 can be provided to limit the movement of hinge means 62, 63 and are respectively formed on upper member 14 and lower member 15 adjacent to but spaced from the respective upper and lower protrusions 36 formed on the central hinge member 35. The space between protrusions 36, formed on the central hinge member 35 and the respective protrusions 37 and 38, provide some "play" at the hinge 40 to permit the upper and lower members 14, 15 of the motion control apparatus 13 to adjust laterally within a range determined by the protrusions for overbite and underbite by a patient using the device. Compensation for upper jaw overbite would be provided for by the hinge 4 by permitting movement shown by the arrow B in FIG. 6. Compensation for underbite of the upper jaw relative to the lower jaw would be provided for by the hinge 40 by permitting the relative movement shown by the arrow A in FIG. 6. The hinge 40 can compensate for overbite or underbite, as well as for badly aligned jaws and teeth within a range which would accommodate a large number of patients or users without requiring special adjustment of the motion control apparatus 13 to accommodate specific individual needs.

FIG. 7 is an enlarged view of the hinge 40 shown in FIG. 6. FIG. 7 shows that the gap between the protrusion 38 on bottom member 15 and the protrusion 36, formed at the bottom of central hinge member 35, has been closed while the gap between the protrusion 37 on top member 14 and, the top protrusion 36 on central hinge member 35, still remains open. The protrusions 36, 37 and 38 can thus act as lateral motion limit control members, which limit the amount of motion between the protrusions 36, 37 and 38. In other words, when the gap between protrusions 36 and 37 is closed, no further movement by that portion of the hinge is possible, whereas, the hinge 40 shown in FIG. 7 can permit further movement between protrusion 37 and upper protrusion 36 of central member 35.

Figure 8:
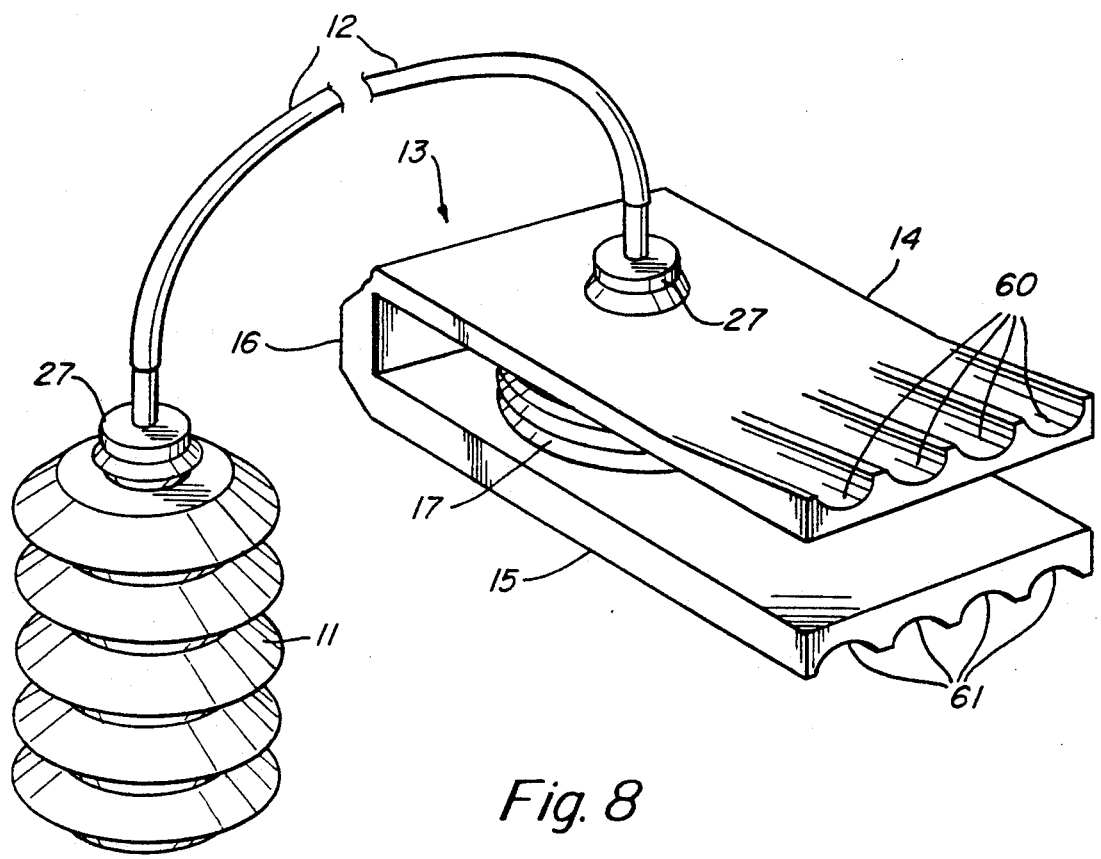
FIG. 8 is a perspective view of a hydraulic mechanism for a hand exerciser of the present invention.

Although the fluid motion device has been described in FIGS. 1-7 with respect to movement of the upper and lower jaws to exercise the temporomandibular joint, it is possible to modify the motion device shown in FIG. 2 for other uses by eliminating the portions thereof for holding the upper and lower teeth. FIG. 8 has fingergrips 60 and 61 on the upper and lower members 14 and 15, which could be used by a person with arthritic hands to exercise the hand and finger joints in the hand. In this configuration, the person would hold the portion of the upper and lower members 14 and 15, furthest from the hinge at finger grips 60 and 61 and squeeze the fluid source 11 to expand the bellows 17, thereby exercising the hand. Similarly the modified device of FIG. 8 could easily be further modified to exercise other small joints such as one or more fingers and toes. For example, for finger exercise, a finger groove or grooves 60 would be placed for example on the top or upper member 14. The unit could then be placed on a table or other support and the user's finger or fingers could be exercised by squeezing the bellows of the fluid source 11. Maximum movement of the finger could be limited by the stop means 32, 33 of FIG. 5 or other suitable means. The position of the bellows 17 between members 14 and 15 can be altered to provide a desired mechanical advantage. For a toe exerciser, for exercising one or more toes, the size of the device shown in FIG. 8 would be scaled down to accommodate one or more toes. The scaled down device could be placed on the floor or other surface. The grips 60 would have one or more toes of a user placed therein and the toe could be exercised by squeezing fluid source 11.

Figure 9:
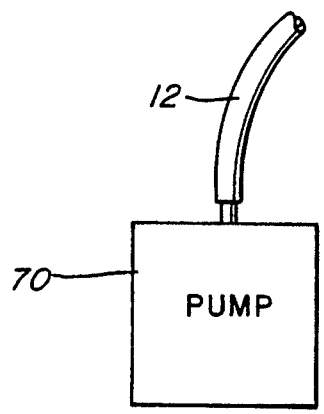
FIG. 9 is a sectional view of an infusion pump which replaces fluid source 11 and FIGS. 1, 2 and 8.

FIG. 9 is a sectional view of a portion of FIGS. 1, 2 and 8 in which the fluid source 11 is replaced by an infusion pump 70 which is connected to flexible tube 12.

While the invention has been described with reference to the drawings and structures and method disclosed herein, it is not confined to the details set forth, and is intended to cover modifications or changes as may come within the scope of the following claims.

I claim

1. A method for controllably exercising the temporomandibular joint which connects the upper and lower jaws of a user, comprising:
    providing first and second members which are coupled together so that at least said first member is movable relative to said second member;
    providing an expandable and contractible fluid reservoir between said first and second members, such that said first and second members will move relative to each other as said expandable and contractible reservoir expands and contracts;
    positioning said first and second members between said jaws of a user to move at least one of said jaws as said expandable and contractible fluid source expands and contracts; and
    periodically expanding and contracting said expandable and contractible reservoir by forcing fluid from a fluid source into said expandable and contractible reservoir, and releasing fluid from said reservoir, thereby moving said at least one of said jaws to exercise said temporomandibular joint.

2. The method according to claim 1, comprising at least partially collapsing said expandable and contractible fluid reservoir after each expansion thereof.

3. The method according to claim 2, wherein elastic means are mounted on said first and second members for contracting said expandable and contractible reservoir after each expansion thereof.

4. The method according to claim 2, comprising controlling the maximum movement of said first and second members relative to each other to thereby control the maximum movement of said temporomandibular joint.

5. The method according to claim 4, wherein said controlling step comprises limiting said maximum relative movement of said first and second members to a preselected maximum value.

6. The method according to claim 1, wherein said expandable and contractible fluid source comprises a bellows.

7. The method according to claim 1, wherein said fluid source is squeezable and said periodic expanding step comprises periodically manually squeezing said fluid source to force fluid into said expandable and contractible fluid reservoir.

8. The method according to claim 1, wherein said upper and lower jaws respectively have teeth ridges, comprising the steps of:
providing hinge means acting as a fulcrum to couple said first and said second members together;
forming upper teeth ridge positioning means on said first member and lower teeth ridge positioning means on said second member;
positioning said upper and lower teeth ridge positioning means on a given side of said fulcrum; and
positioning said expandable and contractible reservoir on said given side of said fulcrum between said hinge and said upper and said lower teeth ridge positioning means.

9. The method according to claim 8, further comprising the step of:
sliding the upper and lower teeth ridge positioning means into the mouth of a user to engage the upper and lower teeth ridges of the user.

10. The method according to claim 1, wherein said fluid source comprises an infusion pump connected to said expandable and contractible fluid reservoir to periodically force fluid thereinto.

11. A method for controllably exercising a small joint which connects two body parts, at least one of said body parts being movable relative to the other, the steps comprising:
holding first and second members together s that at least said first member is movable relative to said second member;
positioning an expandable and contractible fluid reservoir between said first and said second members, such that said members will move relative to each other when said fluid reservoir expands a nd contracts;
positioning at least one of said first and second members to be able to move at least one of said body parts when said fluid reservoir expands and contracts; and
periodically expanding said fluid reservoir by forcing fluid from a fluid source into said fluid reservoir, thereby moving said at least one body part to exercise said small joint.

12. The method according to claim 11, further comprising collapsing said fluid reservoir after each expansion thereof.

13. The method according to claim 12, wherein said first and second members respectively have first and second end portions, the additional steps comprising:
positioning a hinge to movably hold said first end portions of said first and second members together; and
positioning upper and lower teeth ridge portions respectively on said second end portions of said first and second members for engaging teeth of a user.

14. The method according to claim 11, further comprising controlling the maximum movement of said first and second members relative to each other to thereby control the maximum movement of said at least one body part.

15. The method according to claim 11, wherein said expandable and collapsible fluid reservoir comprises a bellows.

16. The method according to claim 11, wherein said fluid source comprises a squeezable member and said periodic expanding step comprises squeezing said squeezable fluid source member to force fluid into said expandable and collapsible fluid reservoir.

17. The method according to claim 11, wherein elastic means are mounted on said first and second members to contract said expandable and contractible fluid reservoir after each expansion thereof.

18. A fluid motion device for exercising the temporomandibular joint which connects the upper and lower jaws, comprising:
a fluid source;
first and second members;
hinge means for holding said first and second members together while permitting at least said first member to move relative to said second member;
an expandable and contractible fluid reservoir positioned between said first and second members;
a fluid channel connecting said fluid source and said expandable and contractible fluid reservoir, said fluid channel providing fluid communication between said fluid source and said fluid reservoir;
said first and second members with said expandable and contractible fluid reservoir therebetween being insertable between said jaws for moving at least one of said jaws when said fluid reservoir expands and contracts; and
means for forcing fluid from said fluid source into said fluid reservoir to expand said fluid reservoir, thereby moving apart said first and second members and moving said at least one of said jaws to exercise said temporomandibular joint.

19. The fluid motion device according to claim 18, further comprising contracting means for contracting said expandable and contractible fluid reservoir after each expansion thereof.

20. The fluid motion device according to claim 19, wherein said contracting means comprises elastic means mounted on said first and second members.

21. The fluid motion device according to claim 18, further comprising controlling means for controlling the maximum movement of said first and second members relative to each other.

22. The fluid motion device according to claim 21, wherein said controlling means comprises limit means for limiting said maximum relative movement to a given amount of relative movement.

23. The fluid motion device according to claim 18, wherein said expandable and contractible fluid reservoir is a bellows.

24. The fluid motion device according to claim 18, wherein said fluid source is squeezable, said fluid source forcing fluid into said fluid reservoir whenever said fluid source is squeezed.

25. The fluid motion device according to claim 18, wherein each of said jaws has teeth ridges further comprising:
upper teeth ridge positioning means mounted on said first member; and lower teeth ridge positioning means mounted on said second member;

said hinge means acting as a fulcrum to hold said first and said second members together;

both said upper and lower teeth ridge positioning means being positioned on a given side of said fulcrum; and said expandable and contractible fluid reservoir being positioned on said given side of said fulcrum between said hinge means and said upper and lower teeth ridge positioning means.

26. The fluid motion device according to claim 18, wherein said fluid source comprises an infusion pump connected to said expandable and contractible fluid reservoir to periodically expand and contract said expandable and contractible fluid reservoir.

27. The fluid motion device according to claim 18, wherein said hinge means comprises a double acting hinge which provides limited lateral movement of said first and second members relative to each other to thereby compensate for overbite or underbite of a user.

28. The fluid motion device according to claim 27, further comprising first and second protrusions formed on said double acting hinge, a third protrusion formed on said first member and a fourth protrusion formed on said second member, said first and third and second and fourth protrusion being positioned to limit lateral and vertical movement of said double acting hinge.

29. The fluid motion device according to claim 18, wherein said fluid channel is permanently sealed.

30. The fluid motion device according to claim 18, wherein said fluid source, said expandable and contractible fluid reservoir, and said fluid communication channel are all formed of a flexible plastic.

31. A fluid motion device for exercising a small joint which connects two body parts, at least one of which is movable relative to the other, comprising:

a fluid source;

first and second members;

hinge means for holding said first and second members together while permitting at least said first of said members to move relative to said second member;

a expandable and collapsible fluid reservoir positioned between said first and second members;

a fluid channel connecting said fluid source and said expandable and contractible reservoir;

means on at least one of said first and second members for positioning and moving at least one of said body parts as said expandable and contractible fluid sources expands and contracts; and means for forcing fluid from said fluid source into said fluid reservoir to expand said fluid reservoir thereby moving said at least one of said first and second members to move said at least one body part to exercise said joint.

32. The fluid motion device according to claim 31, further comprising contracting means for contracting said expandable and contractible fluid reservoir after each expansion thereof.

33. The fluid motion device according to claim 32, wherein said contracting means comprises elastic means mounted on said first and second members.

34. The fluid motion device according to claim 31, further comprising means for controlling the maximum movement of said first and second members relative to each other.

35. The fluid motion device according to claim 34, wherein said controlling means comprises limit means for limiting said maximum relative movement to a given amount of relative movement.

36. The fluid motion device according to claim 31, wherein said expandable and contractible fluid reservoir is a bellows.

37. The fluid motion device according to claim 31, wherein said fluid source is squeezable, said fluid source forcing fluid into said fluid reservoir whenever said fluid source is squeezed.

38. The fluid motion device according to claim 31, wherein said fluid source comprises an infusion pump connected to said expandable and contractible fluid reservoir to periodically expand and contract said expandable and contractible fluid reservoir.

39. The fluid motion device according to claim 31, wherein said hinge means comprises a double acting hinge which provides limited lateral movement of said first and second members relative to each other to thereby compensate for overbite or underbite of a user.

40. The fluid motion device according to claim 39, further comprising first and second protrusions formed on said double acting hinge, a third protrusion formed on said first member and a fourth protrusion formed on said second member, said first and third and second and fourth protrusion being positioned to limit lateral and vertical movement of said double acting hinge.

41. The fluid motion device according to claim 31, wherein said fluid channel is permanently sealed.

42. The fluid motion device according to claim 31, wherein said fluid source, said expandable and contractible fluid reservoir, and said fluid communication channel are all formed of a flexible plastic.

* * * * *